United States Patent
McAllister et al.

(10) Patent No.: US 8,814,880 B2
(45) Date of Patent: Aug. 26, 2014

(54) DEVICE AND METHOD FOR MOUNTING AN OBJECT ON A BONE

(75) Inventors: Craig M. McAllister, Kirkland, WA (US); Steven Jacobson, Dupont, WA (US)

(73) Assignee: Craig M. McAllister, Kirkland, WA (US)

( * ) Notice: Subject to any disclaimer, the term of this patent is extended or adjusted under 35 U.S.C. 154(b) by 1768 days.

(21) Appl. No.: 11/647,921

(22) Filed: Dec. 28, 2006

(65) Prior Publication Data

US 2008/0161814 A1    Jul. 3, 2008

(51) Int. Cl.
*A61B 17/58* (2006.01)

(52) U.S. Cl.
USPC ............................................ 606/104; 606/79

(58) Field of Classification Search
USPC ................ 606/79–80, 104, 53, 83, 86 R, 96; 81/52, 53.1–53.2, 57.39, 431, 441, 81/467–475
See application file for complete search history.

(56) References Cited

U.S. PATENT DOCUMENTS

| 5,255,485 | A | * | 10/1993 | Lemke et al. | 52/410 |
|---|---|---|---|---|---|
| 5,409,486 | A | | 4/1995 | Reese | |
| 5,431,660 | A | | 7/1995 | Burke | |
| 6,203,543 | B1 | | 3/2001 | Glossop | |
| 6,339,977 | B1 | * | 1/2002 | Lee et al. | 81/58.3 |
| 6,554,830 | B1 | | 4/2003 | Chappius | |
| 6,827,722 | B1 | * | 12/2004 | Schoenefeld | 606/104 |
| 6,981,976 | B1 | * | 1/2006 | Schoenefeld | 606/104 |
| 7,013,769 | B2 | * | 3/2006 | Chen | 81/473 |
| 7,150,212 | B2 | * | 12/2006 | Lee | 81/475 |
| 7,197,968 | B2 | * | 4/2007 | Bubel | 81/475 |
| 7,487,700 | B2 | * | 2/2009 | Cutler et al. | 81/475 |
| 2002/0193799 | A1 | | 12/2002 | Chappuis et al. | |
| 2003/0018337 | A1 | | 1/2003 | Davis | |
| 2003/0233098 | A1 | | 12/2003 | Markworth | |
| 2004/0092940 | A1 | * | 5/2004 | Zwirnmann | 606/80 |
| 2004/0199165 | A1 | | 10/2004 | Culbert et al. | |
| 2005/0059975 | A1 | | 3/2005 | Fanger et al. | |
| 2005/0101961 | A1 | | 5/2005 | Huebner et al. | |
| 2005/0119566 | A1 | | 6/2005 | Sasso | |
| 2005/0193870 | A1 | * | 9/2005 | Chen | 81/58.4 |
| 2005/0222575 | A1 | * | 10/2005 | Ciccone et al. | 606/104 |
| 2008/0045970 | A1 | * | 2/2008 | Saidha et al. | 606/104 |

* cited by examiner

*Primary Examiner* — Matthew Lawson (57) ABSTRACT

A device for removable attachment to a bone of a living patient, useful as a mounting support for a trackable part of a computerized surgical navigation system and a method for attaching an object removably to a bone of a living patient. A shaft having a self drilling, self-tapping screw tip can be inserted transversely of the bone and securely screwed into the cortex. A screw drives a sharp-edged sleeve along the shaft to engage the near cortex. A stepping mechanism allows incremental angular movement of a portion of an adjustment mechanism and indicates when the sleeve is securely engaged by resisting further tightening.

12 Claims, 5 Drawing Sheets

DEVICE AND METHOD FOR MOUNTING AN OBJECT ON A BONE

BACKGROUND OF THE INVENTION

The present invention relates to releasably attaching an object to a bone in a living patient, and relates particularly to a device for fastening an object such as a component of a computerized surgical navigation system stably to a large bone such as a femur.

In surgical procedures involving articulated skeletal bone joints, such as knee replacement procedures, it is often helpful to use computer-aided navigation, based on infrared or electromagnetic imaging systems, to locate bones or parts of bones correctly with respect to each other during the procedure. In order to establish and monitor the position of a large bone as a reference for such computer-aided navigation, a reference device must be securely and stably, but removably, mounted on the large bone.

Attachment of objects to bones has been addressed by the prior art, as disclosed, for example, by Glossop U.S. Pat. No. 6,203,543 and Sasso U.S. Patent Application Publication No. US2005/0119566.

In attaching some known devices to a bone as a mounting support for a navigation system reference target or beacon, a screw is inserted transversely through a large bone such as the femur, using a hole drilled entirely through the thickness of the bone. In order to be secure the screw must be long enough to extend beyond a shoulder or other depth-limiting stop far enough to extend into the cortex of the bone on the far side. At the same time, however, the screw should not be so long as to extend unnecessarily beyond the far side of the bone when the shoulder or other stop is seated on the near side of the bone. Accordingly, such a device must be available in various different lengths for use with bones of different sizes. While an estimate can be initially made of the size of a bone, time may be wasted if a mounting device of the wrong size is chosen initially and must be replaced.

Adjustment of some previously available devices to securely support an object such as a part of a navigation system has required separate operations of first drilling and thereafter tapping screw holes in bones, taking more time than is desired during a surgical procedure.

In other devices for anchoring an object to a bone a bone engaging part of the device must be rotated as it is moved through soft tissue surrounding the bone in order to bring that part of the device into engagement against the bone. This rotary motion during movement through the soft tissue causes undesired trauma to the soft tissue and may delay healing in that area.

Adjusting a mounting fastening device to attach it securely to a bone has thus been a difficult and inexact procedure in the past.

What is desired, then, is a device and a method for its use to attach an object securely to a large bone, and to accomplish such attachment without taking an undue amount of time, and with a predictable result, so as to achieve a secure attachment in a device which is readily removable when its presence is no longer required.

SUMMARY OF THE INVENTION

The present invention answers some of the needs mentioned above by providing a device and a method for its use for securely but removably mounting an object on a bone of a living patient.

As an aspect of one embodiment of the device disclosed herein a central shaft may have a screw threaded tip to extend through a bone and be fastened in the cortex of the opposite side of the bone. A bone-engaging member is mounted so as to slide longitudinally along the central shaft without being free to rotate about the shaft and includes a sharpened front end shaped to engage the near side of the bone securely to prevent the central shaft from moving with respect to the bone.

As another aspect of the device, an adjustment mechanism may include a rotatable member mounted on a screw thread formed on the central shaft, so as to push the bone-engaging member along the central shaft until it engages the bone, and the bone-engaging member and the rotatable member may have mutually confronting faces providing for rotation of the driver about the central shaft in discrete angular steps, so as to indicate the force with which the bone-engaging member is urged toward the bone.

As another aspect of the device the central shaft may include a shoulder to limit the depth to which the threaded tip of the central shaft can be engaged in a bone.

As an aspect of another embodiment of the device the central shaft may include a combined drilling and tapping tip and a threaded distal end portion.

A method of use of the device to removably mount an object on a bone in accordance with the present disclosure includes forming a hole of a first size extending into a bone for a first distance, providing threads within the hole, placing a shaft through the hole, and seating the shaft in the bone with a tip in contact with a far side cortex, and thereafter forcing a bone-engaging member longitudinally along the shaft to force a bone gripping front end of the bone-engaging member into gripping engagement in the bone defining and surrounding the first hole, while providing an indication of the force being applied to move the bone-engaging element.

One aspect of the method includes advancing the bone-engaging element by moving it along the shaft by small discretely defined steps.

The foregoing and other objectives, features, and advantages of the invention will be more readily understood upon consideration of the following detailed description taken in conjunction with the accompanying drawings.

DETAILED DESCRIPTION OF EMBODIMENTS

Figures 1, 2, 3, 4:
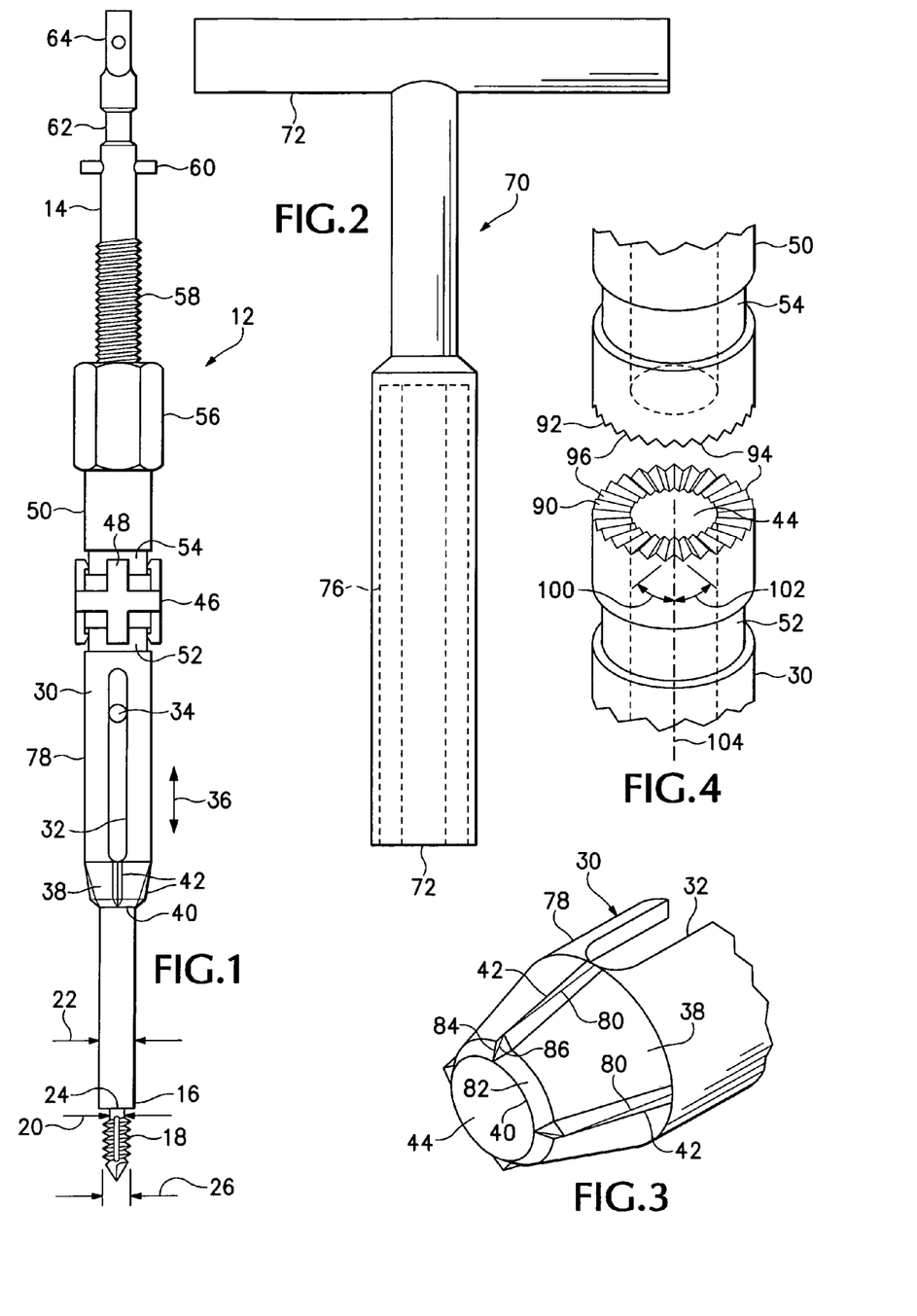
FIG. 1 is a side elevational view of a device for mounting an object removably on a bone which is an exemplary embodiment of the present invention.
FIG. 2 is a side elevational view of a deep socket wrench useful in operating the device shown in FIG. 1.
FIG. 3 is a perspective view of a sharpened front end of a bone-engaging sleeve portion of the device shown in FIGS. 1 and 2.
FIG. 4 is a fragmentary oblique view of adjacent portions of a bone-engaging member and an adjustment mechanism included in the device shown in FIGS. 1 and 2.

Referring now to the drawings which form a part of the disclosure herein, an anchoring device 12, shown in its entirety in FIG. 1, includes a central shaft 14. At a distal end portion 16 of the shaft 14 a threaded tip 18 extends axially. The threaded tip 18 may be of a self-drilling, self-tapping configuration, but need not necessarily be so. The threaded tip 18 may include a central portion with a diameter 20 significantly smaller than a diameter 22 of the central shaft 14, and the central shaft 14 thus may define a shoulder 24. A helical thread defined on the threaded tip 18 may extend radially to a diameter 26 which also should be at least slightly less than the diameter 22 for best performance.

A bone-engaging member in the form of a tubular sleeve 30 is located on the central shaft 14 with a sliding fit. A slot 32 extends radially and longitudinally of the sleeve 30 on at least one side thereof, and a pin 34 mounted in and extending radially from the shaft 14 is engaged in the slot 32, so that the sleeve 30 is unable to rotate about the central shaft 14, although it is able to move longitudinally along the shaft 14 as indicated by the arrow 36. The sleeve 30 has a bone-gripping distal end portion 38, which may be conically tapered to a sharp edge 40, and may have sharpened ribs 42 extending longitudinally and protruding radially from the tapered distal end portion 38. The sleeve 30 defines a central bore 44 which should be large enough to slide easily along the central shaft 14, but small enough to provide only a minimal amount of free radial movement of the sleeve 30 with respect to the shaft 14. A coupling 46 includes one or more legs 48 and interconnects the sleeve 30 with a suitable sleeve position adjusting member, such as a sleeve positioner 50, by engaging circumferential grooves 52 and 54 defined respectively in the sleeve 30 and the positioner 50.

The sleeve positioner 50 may have a hexagonal portion including paired opposite flats 56 spaced a short distance away from the groove 54, or may otherwise be configured to be engaged by a suitable wrench, to rotate the sleeve positioner 50 about the central shaft 14. The sleeve positioner 50 includes internal threads engaged matingly with an external thread 58 defined on the central shaft 14, so that rotating the positioner 50 with respect to the central shaft 14 moves the positioner 50 longitudinally along the central shaft 14.

One or more pins 60 or other protruding members may be provided on the central shaft 14 near its proximal end to receive and mate with or stabilize an object such as a portion of a navigation system (not shown), when such an object is mounted on the anchor device 12. Similarly, a circumferential groove 62 is defined around the central shaft 14 near its proximal end, in order to receive a mating device included in an object to be mounted on the anchor device 12. A square or otherwise suitably shaped proximal tip 64 may be provided on the central shaft 14 to mate with a suitable power-driven wrench to rotate the central shaft 14 during installation of the anchor device 12.

A T-wrench 70 shown in FIG. 2 may include a handle 72, and an open end 74 opposite the handle 72 is open to define a deep socket 76 designed to mate drivingly with the flats 56 or otherwise drivably configured portion of the positioner 50, so as to rotate the positioner 50 with respect to the shaft 14 once the shaft 14 has been installed, as will be explained presently in greater detail.

In one embodiment, the tapered distal end portion 38 of the sleeve 30 may be configured as shown at an enlarged scale in FIG. 3. While a longitudinally middle portion 78 of the sleeve is generally cylindrical, the distal or leading end portion 38 as shown in FIG. 3 is tapered generally conically, but the several longitudinally extending ribs 42 each has a sharp edge 80 directed radially outwardly. For example, there may be four ribs 42 spaced evenly about the tapered distal end 38, although as few as two or as many as six or more ribs 42 may be useful. A leading margin portion 82 of the tapered distal end portion 38 may be ground at a steeper angle to form the sharp edge 40, and each of the ribs 42 may also have a tip of its distal end tapered to coincide with the sharp edge 40 and shaped to include a sharp leading edge 86, so that as the sleeve 30 is moved into contact with a portion of a bone surrounding the central shaft 14 during installation of the anchor device 12, the sharp leading edges 86 and the sharp edge 40 can engage the outer surface of the cortex of the bone and cut slightly into the cortex of the bone so as to engage the ribs 42 in the bone securely to prevent rotation of the sleeve 30, and thus prevent rotation of the anchor device 12 with respect to the bone.

Referring next to FIG. 4, the proximal face 90 of the sleeve 30 and the distal end face 92 of the positioner 50 have sets of opposed radially extending ramp surfaces or facets which engage each other closely at each of several positions of rotation, determined by equally spaced radially extending ridges 94 and 95, and corresponding notches 96 and 97. These permit the positioner 50 to rotate with respect to the central shaft 14 and the sleeve 30, and also limit slippage of the faces 90 and 92 with respect to each other, to provide an indication to a surgeon of when sufficient torque has been applied to the positioner 50 to force the sleeve 30 to engage the tapered end portion 38 securely in a bone yet not extract the threaded tip 18, as will be explained in greater detail presently. It will be understood that the number of ridges 94 and 95 and notches 96 and 97 will determine the incremental angle of rotation between angularly adjacent positions of engagement of the faces 90 and 92 with respect to each other, so that in the embodiment shown in FIG. 4, with 28 ridges 94 shown on the face 90 and 28 ridges 95 on the face 92, positions of stable engagement of the faces 90 and 92 with each other will be separated by slightly less than 13 degrees of rotation of the positioner 50 with respect to the central shaft 14 and the sleeve 30.

In actual practice, the number of ridges 94 and notches 96 may be different from that shown in FIG. 4, and, for example, 40 ridges 94 and 40 notches 96 may be provided, as well as equal numbers of ridges 95 and notches 97, with an angular separation of 9 degrees between adjacent fully mated positions of stability. For example, each ridge 94 or 95 may have height 98 of about 0.010 inch (0.25 mm) at the radially outer surface of the sleeve 30 and the driver 50. While the ridges 94, 95 are shown herein as having equal slopes of 45 degrees at the outer circumferences of the mating faces 90 and 92, with respect to a plane 104 extending diametrically through the sleeve 30 and a particular ridge 94, it will be understood that other combinations of ridge height 98, facet slopes, and angular separation of stable positions may also be chosen. For example, a shallower angle 100 may be chosen in combination with a steeper angle 102 in order to require more torque to be applied to the positioner 50 in one direction of rotation than in the other, in moving from one mated position to the next.

Figure 5:
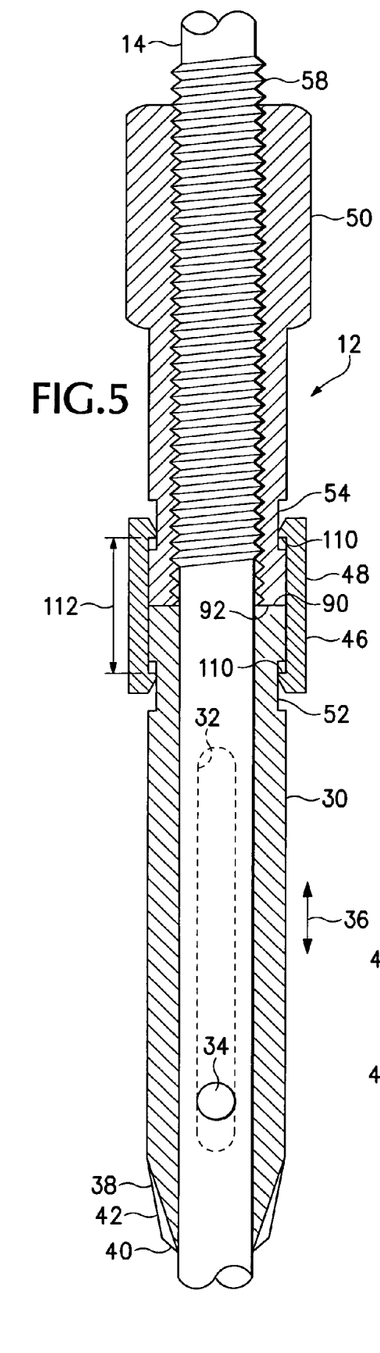
FIG. 5 is a side elevational view of a portion of the device shown in FIG. 1, with portions thereof shown in sectional view taken on a diametrically aligned plane.

As shown in FIG. 5, for example, the coupling 46 has includes four legs 48 interconnected with each other by a belt or ring. Each leg 48 has a catch 110 at each end, extending radially inward and engaged in the respective groove 52 or 54. The catches 110 are separated axially apart from each other along each leg 48 by a distance 112 which is greater than the distance 114 between the surfaces defining the nearer sides, respectively, of the grooves 52 and 54 on the sleeve 30 and the driver 50. The distance 112 is thus great enough to allow the ridges 94 of the faces 90 and 92 to pass by each other freely, with the faces 90 and 92 separated from contact with each other.

The coupling 46, however, prevents the positioner 50 from being separated completely from the sleeve 30, as the catches 110 engage the shoulder surfaces defining the grooves 52 and 54. Turning the positioner 50 in a direction in which the thread 58 moves the sleeve positioner 50 toward the proximal end of the shaft 14 thus brings the sleeve 30 along with the positioner 50, so as to disengage the tapered distal end portion 38 of the sleeve 30 from a bone.

Figure 6:
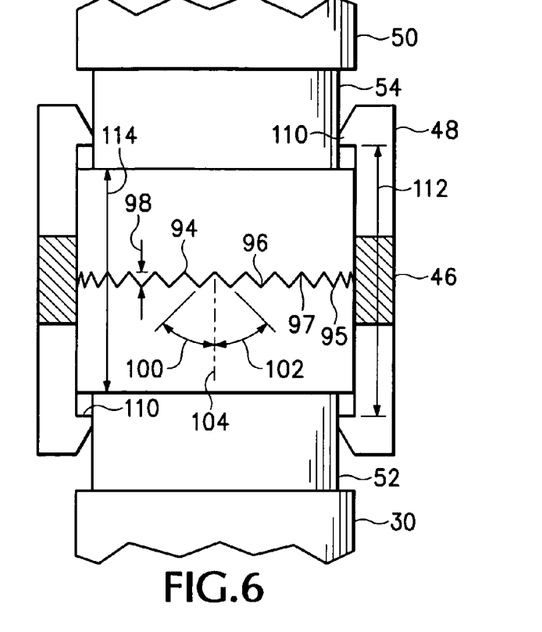
FIG. 6 is a partially cutaway view, at an enlarged scale, of a portion of the coupling arrangement between the bone-engaging sleeve and a sleeve-moving member of an adjustment mechanism of the device shown in FIGS. 1, 4, and 5.
Figure 7:
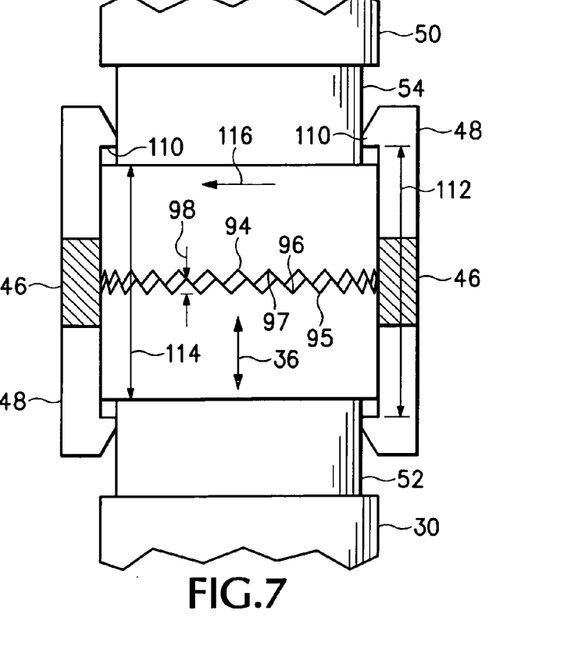
FIG. 7 is a view similar to FIG. 6 showing the coupling with the sleeve-moving member in a different position with respect to the sleeve.
Figure 8:
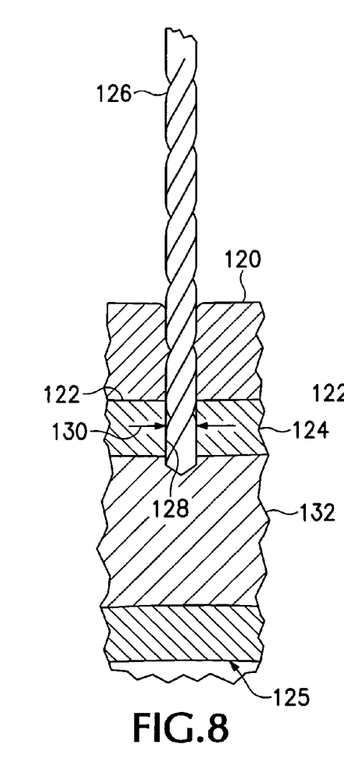
FIG. 8 is a view of a portion of a person's upper leg, showing a first step in the procedure of installing the mounting device shown in FIGS. 1 and 3-7.

As shown in FIG. 7, rotation of the positioner 50 in the direction indicated by the arrow 116 in FIG. 7 causes the ridges 95 of the face 92 of the positioner 50 to ride up along the sloping faces of the ridges 94 of the face 90 of the sleeve 30, which is prevented from rotating with respect to the shaft 14 by the engagement of the pin 34 in the slot 32 as shown in FIGS. 1 and 5. As the opposing ridges 95 pass by the ridges 94 with continued rotation of the positioner 50, any upward pressure on the sleeve 30, that is force urging the sleeve 30 toward the positioner 50, will urge the ridges 94 of the face 90 of the sleeve 30 to slide along the following slope of the ridge 95 of the face 92 of the positioner 50 in an angular stepping manner until the ridges 94 and grooves 97 are again mated as shown in FIG. 6, but with the sleeve 30 in a position slightly further toward the distal end 16 of the shaft 14.

Figures 9, 10:
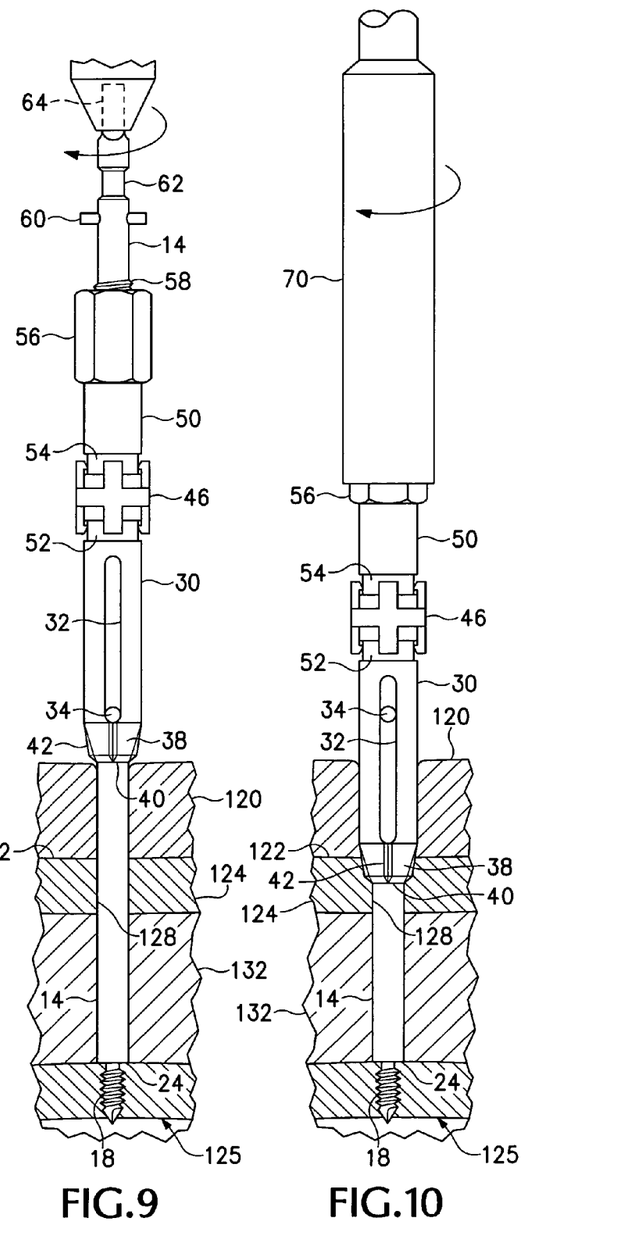
FIG. 9 is a view of the portion of a patient's leg shown in FIG. 8, showing a second step in a procedure of installation of the mounting device.
FIG. 10 is a view similar to FIG. 9, showing performance of a subsequent step in the installation of the mounting device.

The anchor device 12 is utilized, for example, to support a portion of an infrared navigation system on a bone in connection with procedures such as surgical replacement of an injured knee joint, in which case the anchor device 12 is installed in the femur 125 of a patient. To install the anchor device 12, as shown in FIGS. 8-11, for example, soft tissue 120 is dissected and retracted to expose a surface 122 of the anterior cortex 124 of a femur 125 as previously mentioned. A drill 126 may be used to bore a hole 128 having a diameter 130 about equal to or slightly greater than the diameter 22 of the central shaft 14, so that the central shaft 14 can be inserted through the cortex 124 and into the marrow 132 a short distance. The drill 126 is then retracted and, as shown in FIG. 9, the distal end 16 of the central shaft 14 of the anchoring device 12 is inserted into the bone through the hole 128, led by the self drilling, self tapping threaded tip 18. Once the threaded tip 18 engages the cortex 134 on the opposite, posterior, side of the femur 125, the central shaft 14 is rotated to drill a hole 129 into the opposite, posterior, cortex portion 134 of the femur 125, simultaneously tapping the hole 129 and screwing the tip 18 into the posterior cortex 134 until the shoulder 24 at the distal end of the shaft is brought to bear securely against the interior of the posterior cortex 134.

When it is determined by the user, as by an increase in the torque required to turn the central shaft 14, that the threaded tip 18 has drawn the shoulder 24 of the distal end 16 of the central shaft 14 firmly into contact against the interior of the cortex 134 of the opposite or posterior side of the femur 125, rotation of the central shaft 14 is stopped, and a suitable wrench, for example the T wrench 70, is utilized to rotate the positioner 50 about the central shaft 14. The rotation of the positioner 50 about the central shaft 14 is accomplished initially without applying any significant amount of torque to the central shaft 14 itself, but it may be desirable to grasp the sleeve 30 to steady it and resist any tendency of the sleeve and the central shaft 14 to rotate as the positioner 50 is moved along the central shaft 14 by the threads 58. It may also be desirable to urge the sleeve 30 downward along the central shaft 14 to keep the notched opposite faces 90 and 92 of the sleeve 30 and the positioner 50 separated from each other until the tapered distal end portion 38 of the sleeve 30 engages the surface 122 of the femur 125 surrounding the hole 128. As the sleeve 30 moves downward along the central shaft 14 and through the soft tissue surrounding the bone 125, the sleeve 30 is not required to rotate with respect to the soft tissue 120, but only moves downward through the soft tissue without causing unnecessary trauma to the surrounding soft tissue 120.

Once the tapered distal end portion 38 engages the surface 122 of the anterior portion 124 of the cortex of the bone, the tips 84 of the ribs 42 begin to cut into the bone tissue surrounding the hole 128, and by engaging the surrounding bone tissue, the ribs 42 prevent the sleeve 30 from rotating. Because the slot 32 of the sleeve 30 is engaged with the pin 34 on the shaft 14, both the sleeve and the shaft 14 are prevented from rotating with respect to the bone as the wrench 70 continues to rotate the positioner 50 about the shaft 14.

As the distal end portion 38 of the sleeve 30 contacts and penetrates the surface of the bone, the distal end face 92 of the positioner 50 unavoidably is moved into contact against the proximal end face 90 of the sleeve 30, bringing the ridges 95 on the distal end face 92 into contact against the ridges 94 on the proximal face 90 of the sleeve 30. Greater resistance to movement of the sleeve along the shaft 14 naturally requires greater torque to be applied to the positioner 50 to rotate it in the direction of the arrow 116 in the next subsequent position of mating engagement between opposing notches 94 and grooves 96. Thus, as the sharpened tapered distal end 38 is more deeply engaged and the bone-engaging sleeve 30 meets greater opposition from the bone it becomes more difficult to turn the positioner 50 about the central shaft 14. Continued rotation of the positioner 50 drives the sleeve 30 toward the bone 125 forcing the tapered distal end portion 38 of the sleeve 30 into deeper and firmer engagement in the anterior cortex 124 of the bone around the hole 128, but the torque required to turn the handle 72 of the T wrench 70 increases as rotation of the positioner 50 is continued ridge-by-ridge, until the tapered distal end 38 is securely engaged in the bone 125 and further rotation to move the ridges 95 through the next small angular increment, to the next position of mating engagement in the notches 96, requires a noticeable increase in torque to be applied to the wrench 70. At a point before a significant increase in torque would have to be applied to the wrench 70 to move the positioner 50 through the next incremental angle, so that further rotation might risk extracting the threaded tip 18 from the cortex on the far side of the bone, the anchor device 12 will be firmly engaged in the bone 125 and further rotation of the wrench would thereafter not be necessary.

Figure 11:
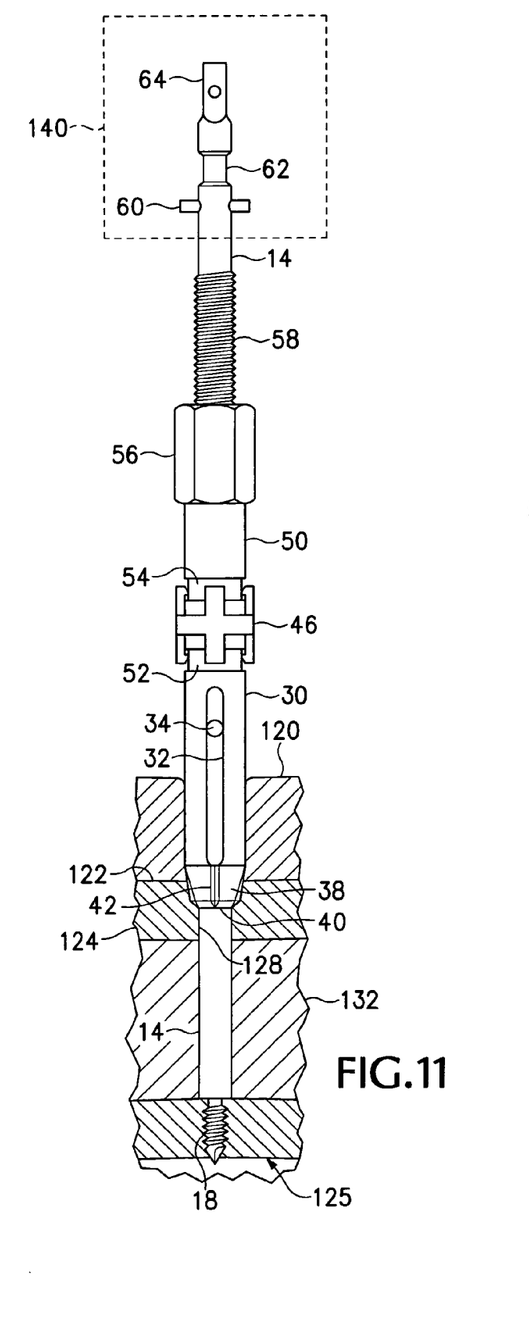
FIG. 11 is a view similar to FIG. 10 showing the mounting device installed and in use to support an object in a fixed position with respect to the patient's leg.
Figure 12:
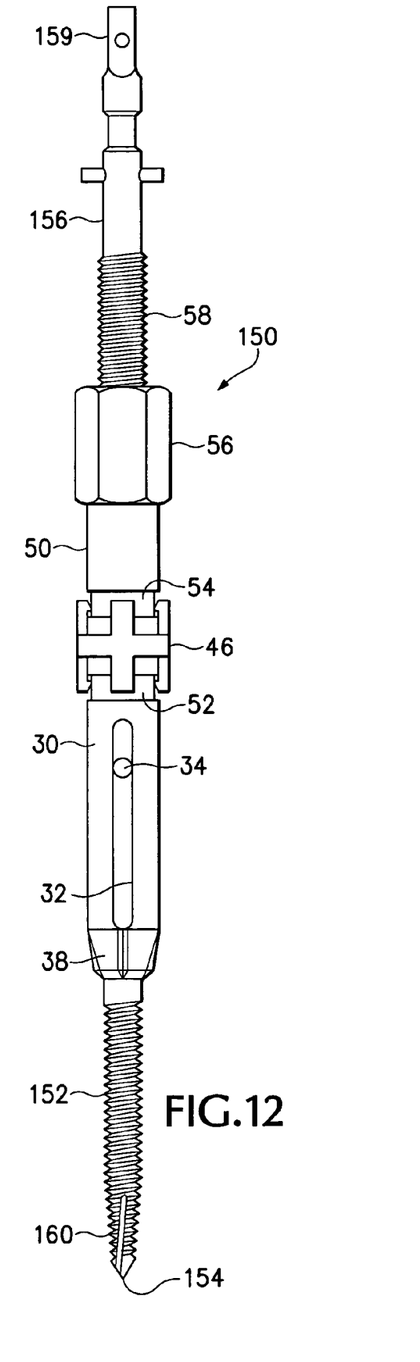
FIG. 12 is a view similar to FIG. 1 showing a device which is an alternative embodiment of the device shown in FIG. 1.

Once firm installation of the anchor device 12 is accomplished, the wrench 70 may be removed and thereafter the anchor is available for use as shown in FIG. 11 to support an object 140 such as in infrared navigation system element, which may be supported by the positioner 50 or otherwise engaged on the proximal end of the central shaft 14, as by being mated with the pins 60 or the groove 62.

As shown in FIGS. 12-15, an alternative anchoring device 150 is similar to the device 12 in many respects, but has a continuous external thread 152 extending proximally from the distal end 154 of its central shaft 156. Instead of having a shoulder such as the shoulder 24 on the central shaft 14 of the device 12 described above, the distal end 154 has a short drilling tip 158 which may be helically fluted. A tap portion 160 which may also be fluted is located adjacent to the drilling tip 158 and is tapered, extending between the drilling tip 158 and the full diameter threaded portion 152 of the central shaft 156.

Figure 13:
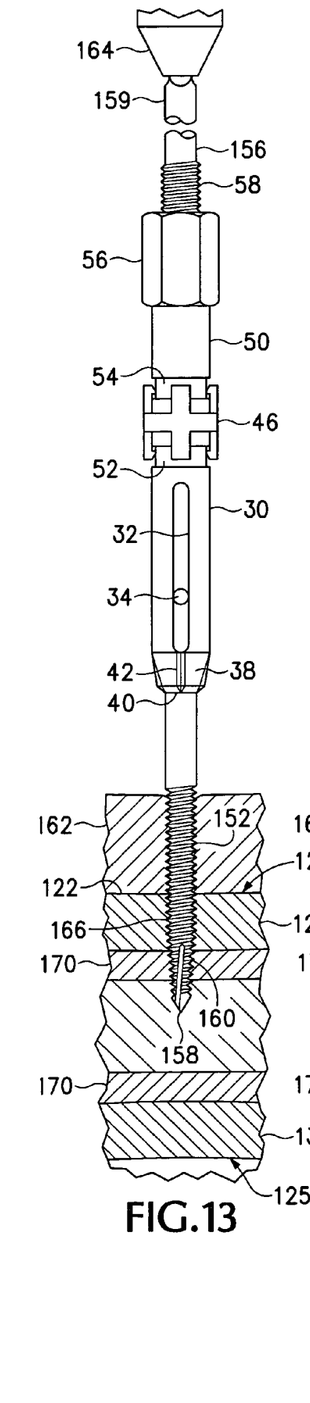
FIG. 13 is a simplified view of a portion of a person's upper leg, showing a first step in the procedure of installing the mounting device shown in FIG. 12.

Use of the anchoring device 150 is somewhat simpler than use of the anchoring device 12, as it is unnecessary to use a separate drill to form an initial hole in the near or anterior cortex 124 of the bone. Instead, as shown in FIG. 13, a simple opening is first cut through the surrounding soft tissue 162 to expose the surface of a bone such as a human femur 125 on which the device 150 is to be installed.

Next with the sleeve positioner 50 and the sleeve 30 retracted toward the proximal end 159 of the central shaft 156, the distal end 154 of the central shaft 156 is inserted through the opening in the soft tissue 162, and the drill tip 158 of the anchor device 150 is brought into contact against the surface 122 of the anterior cortex 124. Using a suitable driver 164 to engage the proximal end 64 of the shaft 156, the shaft 156 is rotated so that the drill tip 158 bores a hole through the anterior cortex 124 and the tap 160 cuts threads 166 in the anterior cortex 124, thus forming a threaded bore through the anterior cortex 124 with the central shaft 156 directed toward the opposite, posterior, side of the femur 125.

Figures 14, 15:
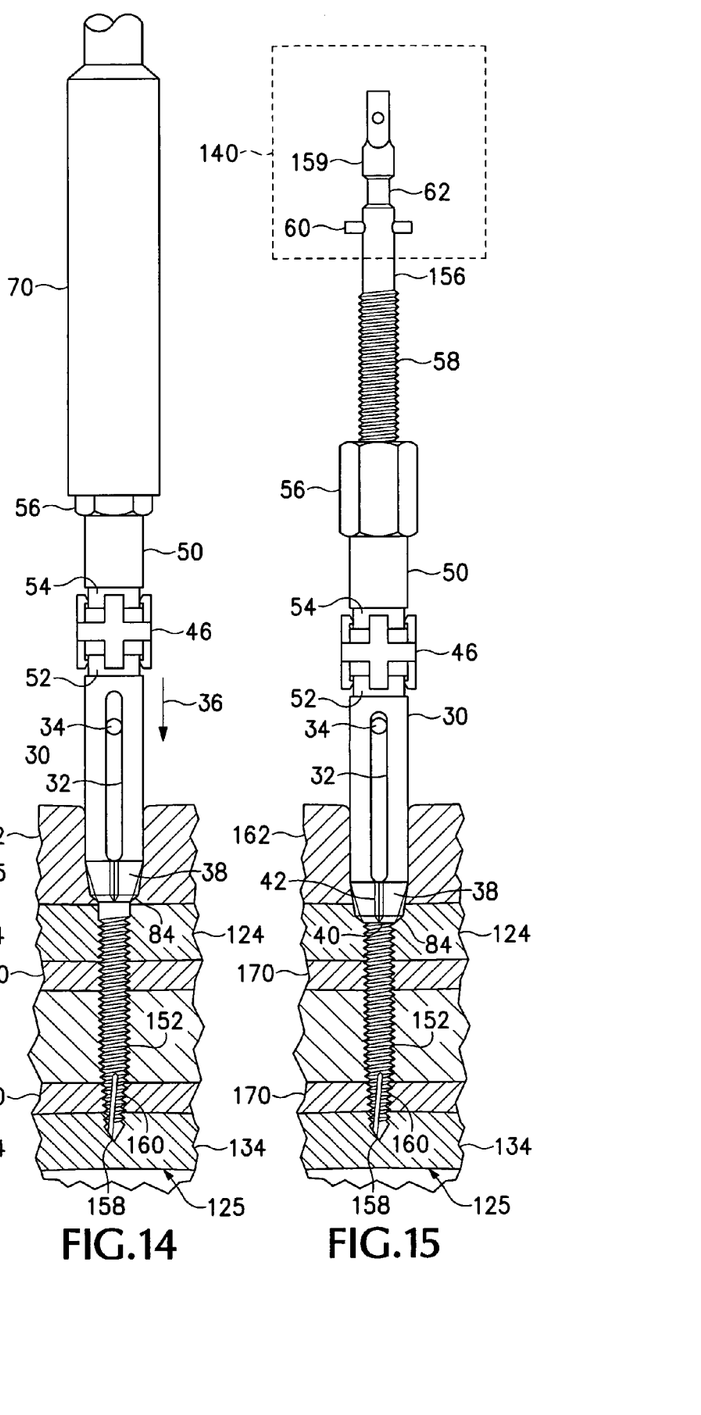
FIG. 14 is a view of the portion of a patient's leg shown in FIG. 13, showing a second step of installation of the mounting device shown in FIG. 12.
FIG. 15 is a further simplified view of the portion of a leg shown in FIG. 14, showing the mounting device after completion of installation.

With continued rotation, the external thread 152 of the central shaft 156 becomes engaged in the threads 166, and rotation of the central shaft is continued, moving the central shaft into the interior of the femur 125, so that the drill tip 158 is eventually brought to bear against the interior surface of the posterior cortex 134, as shown in FIG. 14. Rotation of the central shaft 156 is continued until the drill tip 158 has definitely encountered and may have begun to cut into the cortex 134. In reaching this position, as shown in FIG. 14, the drill tip 158 and tap portion 160 have engaged the spongy or cancellous tissue 170 adjacent the posterior cortex 134, as can be determined by an increase in the effort needed to rotate the central shaft 156.

Rotation of the central shaft 156 is then ceased, and a tool such as the T-wrench 70 is then used, as described before with respect to the mounting device 12, to engage the flats 56 of the nut-like portion of the sleeve positioner 50 and rotate the positioner 50 relative to the central shaft 156, thus driving the sleeve 30 along the central shaft 156 to engage the tapered distal end portion of the sleeve 30 in the cortex 124 of the anterior side of the femur 125. The sleeve positioner 50 is rotated until the slip limiting effect of the mutual contact between the ridges 94, 95 and notches 95, 97 of the faces 92 and 90 of the positioner 50 and the sleeve 30 provides definitely increased resistance to further rotation of the positioner 50, with the tapered distal end portion 38 of the sleeve 30 embedded in the cortex 124 far enough so that the tips 84 and sharp edges 80 of the ribs 42 engage the cortex 124 securely to prevent rotation of the sleeve 30 with respect to the femur 125. As in the anchor device 12, because of the engagement of the pin 34 extending through the central shaft 156 and engaged in the slot 32, the sleeve 30 prevents the central shaft 156 from rotating, so that an object such as a portion of a computer aided navigation system is held securely in its position with respect to the femur 125 when the object is attached to the proximal end 159 of the central shaft 156 in the same manner described above with respect to the central shaft 14 of the anchoring device 12.

As with the device 12, removal from engagement in the femur 125 or other bone is simply the reverse of the procedure for mounting the anchoring device 150, as rotation of the positioning device 50 in the opposite direction along the thread 52 on the proximal end portion of the central shaft 156 first disengages the torque-resisting limited slip latching faces 90 and 92 from each other, while further movement of the positioner 50 along the central shaft 156 causes the coupling 46 to withdraw the distal end portion 38 of the sleeve 30 from engagement in the cortex 124 of the femur. Once the sleeve 30 has been withdrawn from engagement in the surface of the bone the central shaft 156 can be rotated in the opposite direction from that used to install it and thus can be removed from the threaded bore 168.

Because the central shaft 156 can be installed in a bone such as the femur 125 before the sleeve 30 is moved longitudinally along the shaft 156 through the soft tissue and toward the bone, the soft tissue is exposed to only a limited amount of rotation of the sleeve as the central shaft is being installed, and movement of the sleeve along the central shaft is accomplished thereafter without rotation, causing only a minimal amount of trauma to the soft tissue 162 surrounding the sleeve 30.

The terms and expressions which have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A device for mounting an object removably on a bone, comprising:
   (a) a central shaft having a distal end portion;
   (b) a threaded tip included in said distal end portion;
   (c) a bone-engaging member disposed on and movable longitudinally along said central shaft, said bone-engaging member having a bone-gripping distal end;
   (d) wherein said bone-engaging member is a sleeve including a longitudinally-extending slot and wherein a slot-engaging member is perpendicular to said slot and is engaged in said slot;
   (e) an adjustment mechanism mounted on said central shaft and arranged to move said bone-engaging member controllably toward said distal end of said central shaft;
   (f) wherein said adjustment mechanism includes a rotatable member engaged with an external thread on said central shaft;
   (g) wherein said bone-engaging member and said rotatable member form a torque-indicating mechanism;
   (h) wherein said torque-indicating mechanism includes a stepping mechanism;

(i) wherein said stepping mechanism includes each of said bone-engaging member and said rotatable member having complementary and rigidly interlocking teeth; and
(j) wherein said rotatable member when rigidly locked forms a monolithic structure with said longitudinally-extending slot and said slot-engaging member to prevent said sleeve from rotating about said central shaft, locking the sleeve axially.

2. The device of claim 1 including a coupling interconnecting said adjustment mechanism with said bone-engaging member and keeping said adjustment mechanism within a predetermined distance from said bone-engaging member.

3. The device of claim 2 wherein said bone-engaging member includes said sleeve disposed slidably on said central shaft and wherein said sleeve has a groove defined adjacent a proximal end thereof and said adjustment mechanism includes a rotatable member mounted on and rotatable about said central shaft and including a groove defined adjacent a proximal end thereof, and wherein said coupling includes a coupling member disposed adjacent said proximal end of said sleeve and said distal end of said rotatable member and including respective catches engaged in each of said grooves.

4. The device of claim 1 wherein said threaded tip includes a drill.

5. The device of claim 1 wherein said threaded tip includes self-tapping screw threads.

6. The device of claim 1 wherein said threaded tip includes a self-drilling, self-tapping screw.

7. The device of claim 1 wherein said adjustment mechanism includes a rotatable member engaged with an external thread on said central shaft and a rotary coupling connecting said rotatable member with said bone-engaging member.

8. The device of claim 1 wherein said adjustment mechanism includes a rotatable member engaged with an external thread on said central shaft and said bone-engaging member and said rotatable member have respective cooperative elements of a torque-indicating mechanism.

9. The device of claim 1 wherein said stepping mechanism includes corresponding inclined facets defined respectively on the proximal end of the bone-engaging member and the distal end of the rotatable member and wherein corresponding ones of said facets are engageable with each other at selected angles of rotation of said rotatable member.

10. The device of claim 1 wherein said distal end portion includes a shoulder projecting radially outward adjacent said threaded tip.

11. The device of claim 1 wherein said distal end portion is externally threaded along a portion thereof extending in a proximal direction from said threaded tip.

12. The device of claim 11 wherein said threaded tip is self-tapping and gradually increases in diameter toward and merges with said externally threaded portion of said distal end portion.

* * * * *